US012667277B2

(12) United States Patent
Bain

(10) Patent No.: US 12,667,277 B2
(45) Date of Patent: Jun. 30, 2026

(54) SYSTEMS AND METHODS FOR MONITORING BODY ORIENTATION OF A SUBJECT

(71) Applicant: Growth Armor, LLC, Wilmington, DE (US)

(72) Inventor: Michael A. Bain, Costa Mesa, CA (US)

(73) Assignee: Growth Armor, LLC, Wilmington, DE (US)

( * ) Notice: Subject to any disclaimer, the term of this patent is extended or adjusted under 35 U.S.C. 154(b) by 70 days.

(21) Appl. No.: 18/802,889

(22) Filed: Aug. 13, 2024

(65) Prior Publication Data

US 2026/0047778 A1     Feb. 19, 2026

(51) Int. Cl.
*A61B 5/11*          (2006.01)
*A61B 5/00*          (2006.01)
*G08B 21/18*         (2006.01)

(52) U.S. Cl.
CPC ........... *A61B 5/1114* (2013.01); *A61B 5/1126* (2013.01); *A61B 5/6833* (2013.01); *A61B 5/7405* (2013.01); *A61B 5/746* (2013.01); *A61B 2503/04* (2013.01); *G08B 21/182* (2013.01)

(58) Field of Classification Search
CPC ... A61B 5/1114; A61B 5/1126; A61B 5/6833; A61B 5/7405; G08B 21/182
USPC ...................................................... 340/636.1
See application file for complete search history.

(56) References Cited

U.S. PATENT DOCUMENTS

| | | | | |
|---|---|---|---|---|
| 4,493,155 A | * | 1/1985 | Comeau ................. | G01D 5/252 |
| | | | | 33/312 |
| 4,587,741 A | * | 5/1986 | Rorden .................... | G01C 9/06 |
| | | | | 33/366.12 |
| 4,672,753 A | * | 6/1987 | Kent ........................ | G01C 9/20 |
| | | | | 33/366.19 |
| 5,774,055 A | * | 6/1998 | Pomerantz ......... | G08B 21/0208 |
| | | | | 340/517 |
| 6,095,991 A | * | 8/2000 | Krausman ............. | A61B 5/1116 |
| | | | | 600/595 |

(Continued)

OTHER PUBLICATIONS

European Patent Office; EP Extended Search Report; EP 25192754; dated Dec. 19, 2025; 10 pages.

(Continued)

*Primary Examiner* — Zhen Y Wu
(74) *Attorney, Agent, or Firm* — Stetina Garred Brucker & Newboles

(57)          ABSTRACT

Systems and methods are disclosed for determining a body orientation of a subject. A device may be secured to the subject which comprises a housing, a first pair of electrodes in an internal chamber defined by the device, and a conductive material in the internal chamber. The first pair of electrodes may be associated with a first orientation of the device such that when the device is placed in the first orientation, the conductive material is positioned, due to the effects of gravity, to complete a first circuit between the first pair of electrodes. Further pairs of electrodes may be included, each of which may have their circuits completed by the conductive material when the device is placed in a certain orientation. Readings from these pairs of electrodes may be used to determine the subject's body orientation.

18 Claims, 3 Drawing Sheets

(56)          References Cited

U.S. PATENT DOCUMENTS

| | | | | |
|---|---|---|---|---|
| 6,356,203 B1 * | 3/2002 | Halleck | ............. | G08B 21/0288 |
| | | | | 340/517 |
| 6,571,483 B1 * | 6/2003 | Mangerson | ............. | G01C 9/10 |
| | | | | 33/366.26 |
| 9,173,596 B1 * | 11/2015 | Berme | ................ | A61B 5/0024 |
| 9,414,784 B1 * | 8/2016 | Berme | .................... | A61B 5/01 |
| 10,383,527 B2 * | 8/2019 | Al-Ali | ...................... | A61B 5/01 |
| 2014/0331793 A1 * | 11/2014 | Suzuki | ................. | G01L 1/2287 |
| | | | | 156/280 |
| 2016/0374608 A1 * | 12/2016 | Dugan | ................... | A61B 5/746 |
| | | | | 600/301 |
| 2019/0151705 A1 * | 5/2019 | Pandit | ............... | A63B 21/0442 |

OTHER PUBLICATIONS

Defloor T., et al; "The effect of various 4 combinations of turning and pressure reducing devices on the incidence of pressure ulcers", International Journal of Nursing Studies, Pergamon, Amsterdam, NL, vol. 42, No. 1, Jan. 1, 2005 (Jan. 1, 2005), pp. 37-46, XP027736736, ISSN: 0020-7489; 10 pages.

* cited by examiner

SYSTEMS AND METHODS FOR MONITORING BODY ORIENTATION OF A SUBJECT

CROSS-REFERENCE TO RELATED APPLICATIONS

Not Applicable

STATEMENT RE: FEDERALLY SPONSORED RESEARCH/DEVELOPMENT

Not Applicable

BACKGROUND

1. Technical Field

The present application relates to monitoring a body orientation of a subject. More specifically, the present application relates to devices containing a conductive material and pairs of electrodes which are securable to a subject such that the conductive material completes a circuit between a particular pair of electrodes, depending on a body orientation of the subject.

2. Related Art

Pressure injuries, which also go by the names of pressure ulcers or bed sores, occur when pressure is applied to the skin over a long period of time. These injuries are most prevalent for patients recovering from medical conditions that leave them bedridden, with most cases happening on the heels of the feet, shoulder blades, back of the head, and tailbone area. An easy way to prevent these injuries from arising is to turn a patient and change their body orientation every once in a while, with most hospitals using a standard of doing so once every two hours.

It can, however, be just as easy for a hospital technician to forget to do this. The use of timed alarms has not proven to be a surefire reminder to these technicians, as they have serval duties which can distract them from this duty. Smith & Nephew PLC, headquartered in England, UK, provides a product called the LEAF Patient Monitoring System for monitoring a patient's body orientation and notifying nearby staff when the patient needs to be turned. However, this device measures the patient's movement with an accelerometer, which consumes a relatively large amount of energy, which drives up the cost of the device and drains the battery quite quickly. As such, it can be seen that new and improved systems and methods for monitoring the body orientation of a subject are needed and desired in the art which can be used for long periods of time and are cheaper to manufacture.

BRIEF SUMMARY

To solve these and other problems, the present disclosure provides systems and methods for monitoring a subject's body orientation. A device for monitoring a body orientation of a subject the device may comprise a housing, a first pair of electrodes in an internal chamber defined by the device, the first pair of electrodes being associated with a first orientation of the device, and a conductive material in the internal chamber, the conductive material completing a first circuit between the first pair of electrodes when the device is placed in the first orientation. In particular, gravity may cause the conductive material to move through the internal chamber and be placed in contact with the pair of electrodes when the device is placed in this first orientation. This device could further comprise a second pair of electrodes in the internal chamber, the second pair of electrodes being associated with a second orientation of the device, the conductive material competing a second circuit between the second pair of electrodes when the device is placed in the second orientation. To measure further orientations, a third, fourth, fifth, etc. pair of electrodes can be included for a third, fourth, fifth, etc. orientation of the device. By securing this device to a subject and correlating the device's orientation with certain body orientations of that subject, one can monitor the body orientation of the subject based on the electrode readings.

If multiple pairs of electrodes are present, they may be spaced from one another such that a rotation of the device on an axis of rotation by at least 30 degrees, at least 60 degrees, or at least 90 degrees is necessary to transition the device from one orientation to a second orientation. The pairs of electrodes can be disposed on an internal surface which bounds the internal chamber. This internal surface can have a circular geometry.

The device may further comprise a battery and an alarm. The alarm could be operative to sound in response to one or more of: the first circuit being completed for at least a prescribed portion of a prescribed time period, a battery life of the battery falling below a threshold value. The prescribed time period is at least 2 hours, and the prescribed portion of that time period could be at least 90%.

Methods of using this device may comprise securing the device to a subject such that the device becomes placed in the first orientation when the subject is in a first body orientation and determining the body orientation of the subject based on a reading from the first pair of electrodes. The subject may be a human, and in certain cases this human may be no more than three years old. The device can be secured to an anatomical region of the human, which may rely on the use of adhesive on the subject. The device itself may comprise this adhesive, such as on a back thereof.

After an alarm of the device sounds in response to a circuit being connected for at least a prescribed portion of a prescribed time period, the method could include a step of changing a body orientation of the subject. The device can include a communication link for transmitting a signal based on the electrode readings of the device. If necessary, this signal may cause the external device to trigger a warning, which could indicate that the subject needs attention, that the device needs to be replaced, or the device's battery is running low.

All of these embodiments are contemplated to be within the scope of this disclosure. These and other embodiments will become readily apparent to those skilled in the art form the following detailed description of the preferred embodiments having reference to the attached figures, the disclosure not being limited to any particular preferred embodiment.

BRIEF DESCRIPTION OF THE DRAWINGS

These and other features and advantages of the various embodiments disclosed herein will be better understood with respect to the following description and drawings, in which like numbers refer to like parts throughout, and in which.

Common reference numerals are used throughout the drawings and the detailed description to indicate the same elements.

DETAILED DESCRIPTION

Systems and methods are disclosed with which a patient's body orientation can be monitored. A device comprising a housing, one or more pairs of electrodes in an internal chamber defined by the device, and a conductive material in the internal chamber can be secured to a subject, such as a patient in a hospital bed. Due to the effects of gravity, the conductive material may, depending on the device's orientation, push up against a pair of electrodes and complete a circuit therebetween. The device's orientation, and which circuit is completed in that orientation, can be correlated to one or more body orientations of the subject. Electrode readings, which can come in the form of simple, binary YES/NO data can be recorded to determine the subject's body orientation. The device can be configured to sound an alarm or trigger a warning on an external device if a threshold is reached, such as the subject being placed in a certain body orientation (e.g., facedown) or if the subject has remained in a certain body orientation for a prescribed portion of a prescribed period of time, such as 90% or more of at least a 2 hour period. Such a device may have improved battery life and usability when compared to prior body orientation measuring devices.

The present disclosure encompasses various embodiments of systems and methods for monitoring a body orientation of a subject. The subject matter disclosed herein will be best understood in view of the drawings, in which exemplary embodiments of the systems and methods disclosed herein are shown. The drawings are intended to illustrate examples and are thus not intended to limit the systems and methods they embody. The detailed description set forth below in connection with the appended drawings is intended as a description of several currently contemplated embodiments and is not intended to represent the only form in which the disclosed subject matter may be developed or utilized. This description sets forth the functions and features in connection with the illustrated embodiments. It is to be understood, however, that the same or equivalent functions may be accomplished by different embodiments that are also intended to be encompassed within the scope of the present disclosure. It is further understood that the use of relational terms such as first and second and the like are used solely to distinguish one from another entity without necessarily requiring or implying any actual such relationship or order between such entities.

Figure 1:
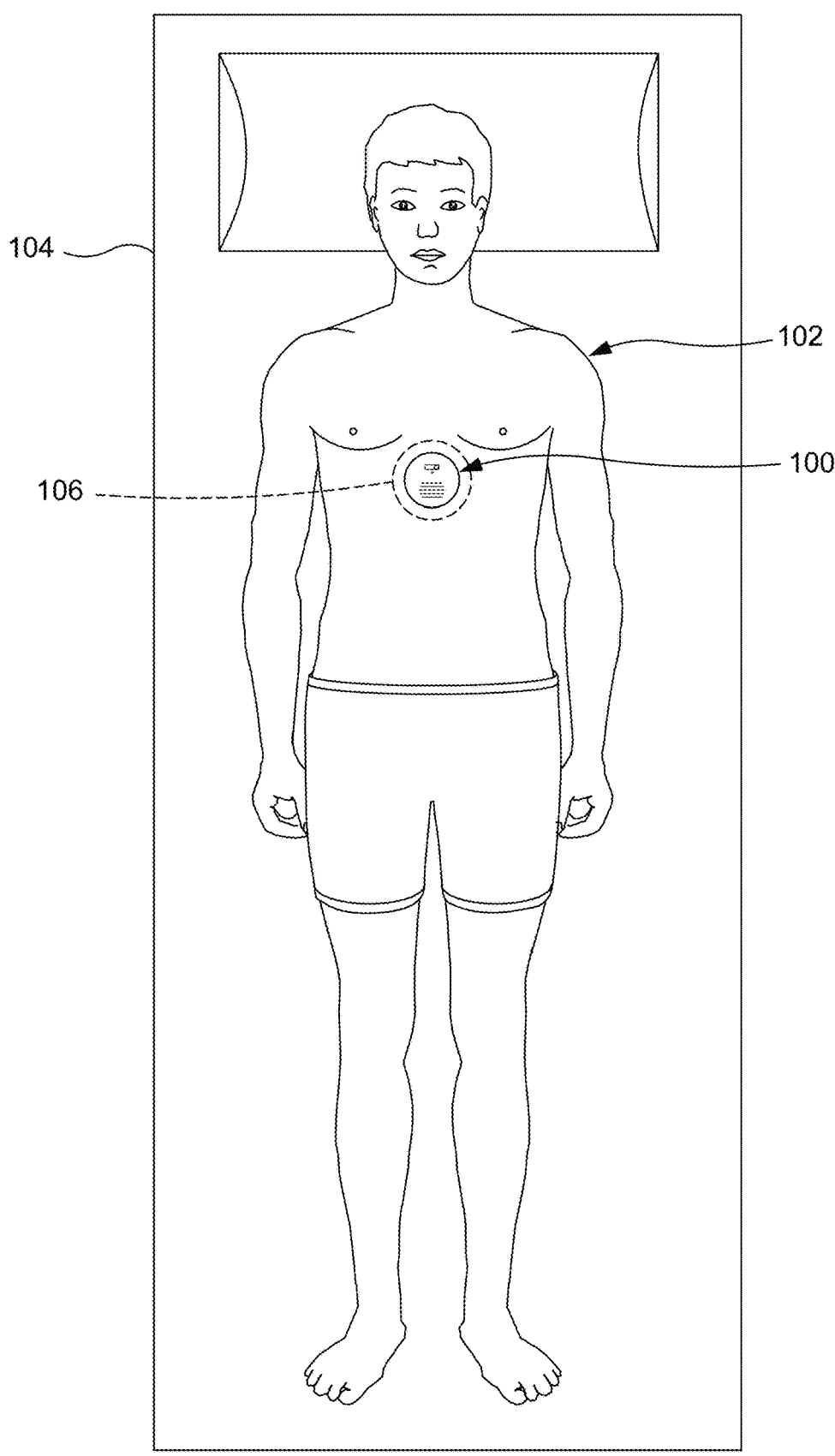
FIG. 1 is an adult subject having a first embodiment of a device according to the present disclosure secured to them.
Figure 2:
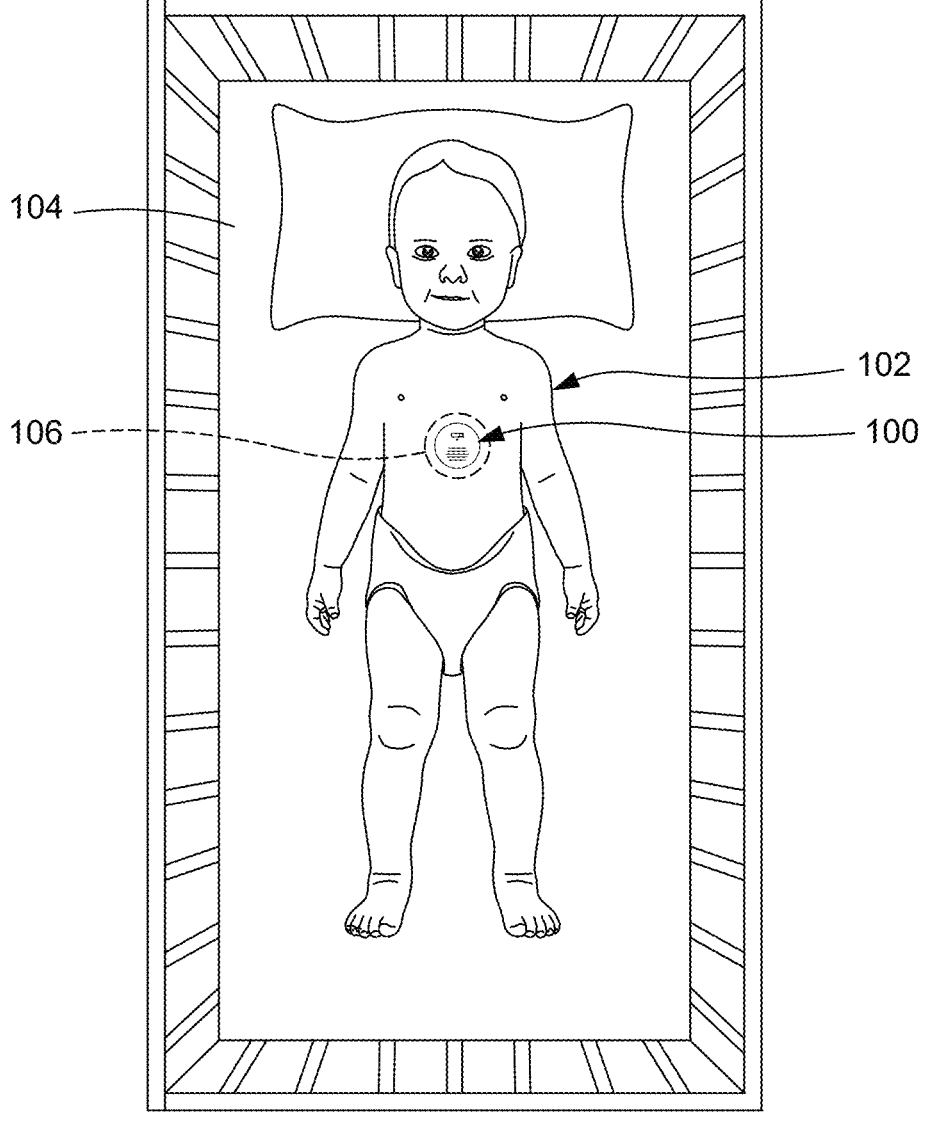
FIG. 2 is a child subject having a second embodiment of a device according to the present disclosure secured to them.

Referring first to FIGS. 1 and 2, adult and child subjects having a first embodiment of a device according to the present disclosure secured to them is shown. A device 100 may be employed to monitor the body orientation of a subject 102. The subject 102 could be resting or sleeping on a bed 104, and in some embodiments the subject 102 could be a hospital patient on a hospital bed, a baby (i.e., a human no more than three years old) in a cradle at home, or an animal such as a dog. In such contexts, the device 100 may help to prevent pressure injuries (i.e., bed sores, pressure sores, decubitus ulcers) and/or prevent the subject from laying facedown for an extended period of time (which could prevent injuries in children such as sudden infant death syndrome or SIDS). A device 100 would preferably be secured to the subject 102 such that a change in body orientation of the subject 102 causes the device 100 to have a similar change to its own orientation. This could be achieved by securing the device 100 to an anatomical region 106 like the chest or lower neck of a subject 102; to secure the device 100 in this manner, the device 100 may have a skin-friendly adhesive and/or an adhesive tape could be used to affix the device 100 to the anatomical region 106. Alternatively, a device 100 could be attached to an implement the subject 102 could be wearing, which could come in the form of a collar or tight t-shirt. Whichever option is chosen, care may be taken to ensure the orientation of the device 100 properly and appreciably changes as the body orientation of the subject 102 changes. This could depend on which body orientations one wishes the device 100 to detect and how many different body orientations a particular device 100 is capable of detecting.

Figures 3, 4, 5, 6:
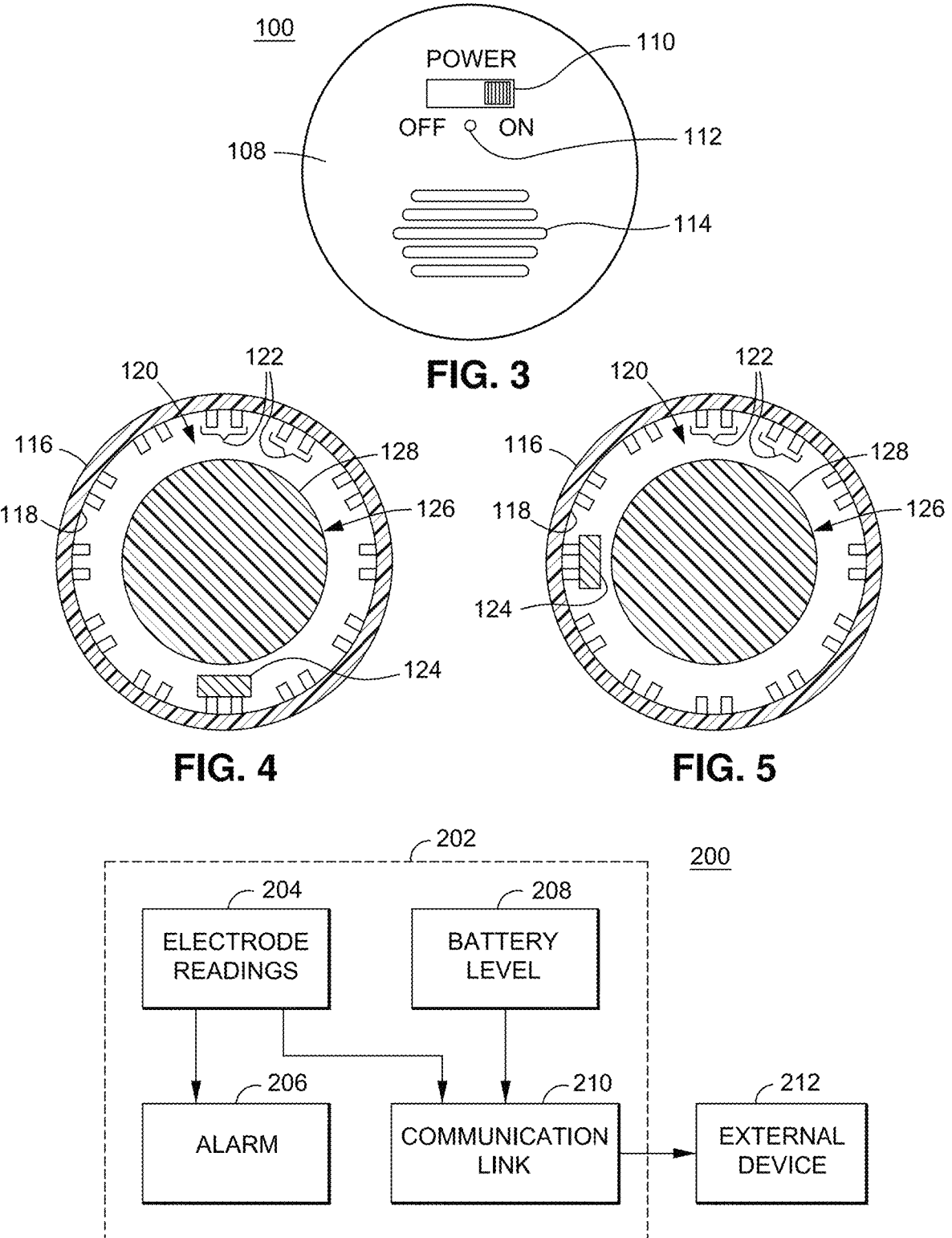
FIG. 3 is a front view of the first embodiment of the device of FIG. 1 according to the present disclosure.
FIG. 4 is a front cross-sectional view of the first embodiment of the device of FIG. 2 at a first orientation.
FIG. 5 is a front cross-sectional view of the first embodiment of the device of FIG. 2 at a second orientation.
FIG. 6 is an exemplary body orientation monitoring system architecture according to the present disclosure.

Looking now to FIG. 3, a front view of a first embodiment of a device according to the present disclosure is shown. A device may be comprised of a housing 108 which may be sized and shaped for a particular application; for example, the housing 108 could be larger or smaller if it is to be used on an adult or child respectively. Ideally, the housing 108 would have a generally smooth geometry without edges so that it may not irritate or harm a subject the device 100 is secured to. Along similar lines, the device 100 would preferably be lightweight, small, planar, and unobtrusive to reduce discomfort a subject 102 may experience with a larger device.

The housing 108 may contain a battery to power the device 100. To turn on the device 100, one may interact with a power switch 110, which could come in the form of a sliding switch, a button, etc. A power light 112 could be included to indicate if the device 100 is turned on or not. The power light 112 may remain unlit when the device 100 is powered off. When the device 100 is turned on, the power light 112 may be lit, although depending on the configuration of the device 100, the state of the power light 112 could change in response to the current battery level. For example, if the battery level is above a threshold value, the power light 112 could emit light in a first color, such as green, but when the battery level falls below that threshold value (e.g., 20%, 15%, or 10% of the maximum battery level), the power light 112 could then emit light in a second color, like red. This could indicate that one should replace the device 100 with another device 100, replace the battery in the device 100, or recharge the battery in the device 100. The power light 112 could, independently in each high-battery level and low-battery level conditions, constantly emit light or periodically emit light, such as a flash or pulse of light every 5 seconds, 10 seconds, etc. To keep power consumption low and allow a device 100 to remain activated over longer periods of time, the latter configuration is preferred. In alternative embodiments, there may be more than one power light 112, with one power light indicating whether or not the device 100 is on or off and another power light indicating that the battery level has fallen below a threshold value.

The housing 108 could define alarm vents 114 through which sounds generated by an alarm of the device 100 may be transmitted through the surrounding environment. This alarm could sound in response to the device 100 being placed in a particular undesired orientation, the device 100 remaining in a particular orientation for a prescribed portion of a prescribed period of time, and/or a battery level falling below a threshold. In this last case, and if the device 100 has a power light 112 which responds to the battery level falling below a first threshold value as described above, the alarm could sound when the battery level falls below a second, lower threshold value. In this respect, the alarm could act as a second layer of safety, as in the event that one doesn't notice or doesn't properly react to an indication of a low battery level from the power light 112, the alarm could sound to remind or alert them to react before the battery fully drains. The sound emitted from the alarm may be distinct for each circumstance the alarm is designed to sound for, such that one can be made aware of which condition requires their attention.

Turning now to FIGS. 4 and 5, a front cross-sectional view of the first embodiment of the device of FIG. 2 at a first orientation and a second orientation respectively are shown. A device 100 can be configured to defines an internal chamber 120. The internal chamber 120 may be bounded by an internal surface 118, and this internal surface 118 could be part of the housing 108 such that an external surface 116 of the housing is associated with the external environment while the internal surface 118 is associated with the internal chamber 120 (although the internal surface 118 does not necessarily need to be part of the housing in this manner). The volume of the internal chamber 120 may be restricted by a filling 126, which could assist in limiting the movement of the conductive material 124, as will be discussed momentarily.

One or more pairs of exposed, disconnected electrodes 122 may be disposed within the internal chamber which may be activated when the device 100 is turned on. Each pair of electrodes 122 may correspond to a distinct orientation of the device 100. A conductive material 124 may be present in the internal chamber 120 which can complete a circuit between each pair of electrodes 122. The circuit which the conductive material 124 completes may depend on the orientation of the device 100 and the effect of gravity on the conductive material 124. With respect to the depiction shown in FIG. 3, for example, the conductive material 124 can connect the circuit between a first pair of electrodes 122 at the bottom of device 100 when the device is in a first orientation (e.g., when the device is secured to a subject who is laying on their back). When the device 100 then is placed in a second orientation (e.g., when the device is secured to a subject who is laying on their right-hand side), the conductive material 124 may move through the internal chamber 120 to then complete a circuit between a new pair of electrodes 122, such as the one on the left shown in FIG. 4.

The pairs of electrodes 112 can be disposed on the inner surface 118 bounding the internal chamber 120. Preferably, this inner surface 118 has a smooth geometry (e.g., circular, oval, parabolic, etc.) so that the conductive material 124 has no trouble or minimal trouble moving from one pair of electrodes 122 to the next when the orientation of the device 100 is changed; square or rectangular geometries, on the other hand, may create a risk of the conductive material 124 becoming stuck on an edge or turn and not properly completing a circuit of a particular pair of electrodes 122. In a similar vein, the pairs of electrodes 122 may be unobtrusive so that they don't hinder the movement of the conductive material 124. The pairs of electrodes 122 shown in FIGS. 3 and 4 are intentionally made large for ease of reference, but in actual embodiments the pairs of electrodes 122 may barely protrude from the internal surface 118. Pairs of electrodes 124 may alternatively or additionally be placed on a surface 128 of the filler 126, although these pairs of electrodes 122 may need to be configured differently (e.g., protrude out further) from those disposed on the inner surface 118, as gravity may not assist in push the conductive material 124 against those pairs of electrodes 122. The filling 126 may intentionally limit the open volume of the internal chamber 120 so that the conductive material 124 is guided through a particular path when the orientation of the device 100 changes.

Pairs of electrodes 122 can be included or excluded in a device 100 as desired. For example, if there is only one general orientation of the device 100 at interest, only a first pair of electrodes 122 may be present. This could be the case if the subject is a baby sleeping in a crib at their home and one only wishes to be made aware when the baby lies facedown to prevent, for example, sudden infant death syndrome (SIDS). A second, third, fourth, etc. pair of electrodes 122 can be included should one desire to detect or monitor a second, third, fourth, etc. orientation of the device 100. Pairs of electrodes 122 may be spaced from one another so that they correspond to a particular orientation of the device 100 and the conductive material 124 may complete the circuit for the corresponding pair of electrodes 122 when the device 100 is in that particular orientation. The pairs of electrodes 122 may be spaced such that the device 100 needs to be rotated a certain amount in order to transition from a first orientation to a second orientation. For example, it may require at least a 30 degree, 60 degree, or 90 degree rotation on an axis of rotation for the device 100 to go from a first orientation, in which the conductive material 124 completes the circuit of a first pair of electrodes 122, to a second orientation, in which the conductive material 124 completes the circuit of a second pair of electrodes 122. The size of the conductive material 124, the spacing between pairs of electrodes 122, and the spacing between the two electrodes which make up a pair of electrodes 122 may be configured such that the conductive material 124 is only capable of being in contact with one or two electrodes of a particular pair of electrodes 122 for any given orientation of the device 100.

The conductive material 124 can be any type of conductive material familiar to those skilled in the art, including metals, electrolytes, semiconductors, nonmetallic conductors like graphite and conductive polymers, and more. The conductive material 124 could be in a solid or liquid state when exposed to an ambient temperature the device 100 will be exposed to for its intended purpose. Preferably, the conductive material 124 would be inert and maintain its conductive properties for the anticipated lifespan of the device 100 (which may be related to the battery life of a battery of the device 100).

Looking now to FIG. 6, an exemplary body orientation monitoring system architecture according to the present disclosure is shown. A body orientation monitoring system architecture 200 may include a device system architecture 202 (which may represent the functionality of the device 100). Electrode readings 204 may be received, for example, a processor when the conductive material 124 completes a circuit for a certain pair of electrodes 122. Electrode readings 204 can take the form of a binary YES/NO measurement of each pair of electrodes 122 such that if the conductive material 124 is completing a circuit for a certain pair of electrodes 122, a YES can be recorded for that pair of electrodes and a NO can be recorded for the remaining pairs of electrodes. If there is only one/a limited range of body orientations at interest, the conductive material 124 may not complete any circuit of the pairs of electrodes 122, in which case a NO can be recorded for each pair of electrodes 122. The electrode readings 204 can be continuously monitored or recorded once over regular time intervals (e.g., an electrode reading can be taken once every 5 minutes, once every 10 minutes, and so on). From these electrode readings 204, one can determine the body orientation of a subject, which could come in the form of finding a particular body orientation of the subject or finding that the subject is not in a particular body orientation. The binary nature of the electrode readings 204 may keep power consumption of the device 100 low and allow it to be used for longer periods of time without needing to replace the device 100, replace the battery, or recharge the battery.

If the electrode readings 204 reach a threshold condition, an alarm 206 of the device 100 may be sounded. This threshold condition could be the circuit of a particular pair of electrodes 122 being complete (which could be associated with the subject being facedown), a particular pair of electrodes 122 maintaining a YES measurement over a certain period of time (e.g., 2 hours), and/or a certain percentage of the YES measurements being from a particular pair of electrodes 122 over a period of time (e.g., 90% or more of the measured readings being YES from a particular pair of electrodes over a 2-hour period). The sound emitted by the alarm for a certain threshold condition may vary from another, such that one can react to the alarm 206 accordingly. 2 hours is the threshold hospitals typically use for rotating a patient in a hospital bed to prevent pressure injuries. Therefore, this device 100 can be used to notify a hospital technician when a bedridden patient has remained in the same body orientation or mostly remained in the same body orientation over a 2-hour period, after which the technician may change the patient's body orientation accordingly.

The device 100 could include a communication link 210 for communication with an external device 212. Ideally, the communication link 210 would comprise a wireless connection with the external device 212. The external device 212 could be a computer or mobile device which can receive the electrode readings 204. If the device 100 is being used at a hospital, the electrode readings 204 can be stored and saved under the subject's patient file for future reference. If a threshold condition is reached for the measured electrode readings 204 (such as those which trigger the alarm 206 as described above), the external device 212 may recognize this and trigger a warning. This system could act in place of the alarm 206 (in which case the alarm 206 could be excluded from the device 100) or it can be present alongside the alarm 206 and act as an extra layer of safety. If both the alarm 206 and communication link 210 are present in a device 100, and should the communication link 210 become disconnected from the external device 212, the alarm 206 may sound indicating that such has occurred. The battery level 208 of a battery of the device 100 can also be transmitted by a communication link 210 to an external device 212 so as to inform one of when the battery will need to be replaced/recharged or the device 100 itself replaced.

The above description is given by way of example, and not limitation. Given the above disclosure, one skilled in the art could devise variations that are within the scope and spirit of this disclosure. Further, the various features of the embodiments disclosed herein can be used alone, or in varying combinations with each other and are not intended to be limited to the specific combination described herein. Thus, the scope of the claims is not to be limited by the illustrated embodiments. Additional modifications and improvements of the present disclosure may also be apparent to those of ordinary skill in the art. Thus, the particular combination of parts and steps described and illustrated herein is intended to represent only certain embodiments of the present subject matter and is not intended to serve as limitations of alternative devices and methods within the spirit and scope of this disclosure.

What is claimed is:

1. A device for monitoring a body orientation of a subject, the device comprising:
   a housing;
   a first pair of electrodes in an internal chamber defined by the device, the first pair of electrodes being associated with a first orientation of the device;
   a second pair of electrodes in the internal chamber, the second pair of electrodes being associated with a second orientation of the device;
   a conductive material in the internal chamber; and
   a filling in the internal chamber configured to restrict an open volume of the internal chamber such that the conductive material is guided through a particular path defined by the filling;
   wherein effects of gravity cause the conductive material to be guided through the particular path such that a first circuit between the first pair of electrodes is completed by the conductive material when the device is oriented in the first orientation;
   wherein effects of gravity cause the conductive material to be guided through the particular path such that a second circuit between the second pair of electrodes is completed by the conductive material when the device is oriented in the second orientation;
   wherein effects of gravity cause the conductive material to be guided through the particular path such that the first circuit between the first pair of electrodes is not completed when the device is not oriented in the first orientation; and
   wherein the effects of gravity cause the conductive material to be guided through the particular path such that the second circuit between the second pair of electrodes is not completed when the device is not oriented in the second orientation.

2. The device of claim 1, wherein the first and second pairs of electrodes are spaced from one another such that a rotation of the device on an axis of rotation by at least 30 degrees is necessary to transition the device from the first orientation to the second orientation.

3. The device of claim 1, wherein the first and second pairs of electrodes are disposed on an internal surface which bounds the internal chamber.

4. The device of claim 1, wherein the device further comprises:
   a battery; and
   an alarm;
   wherein the alarm is operative to sound in response to one or more of: the first circuit being completed for at least a prescribed portion of a prescribed time period, a battery level of the battery falling below a threshold value.

5. The device of claim 4, wherein the prescribed time period is at least 2 hours.

6. A method of monitoring a body orientation of a subject, the method comprising the step of:
   providing a device comprising:
   a housing;
   a first pair of electrodes in an internal chamber defined by the device, the first pair of electrodes being associated with a first orientation of the device;

a second pair of electrodes in the internal chamber, the second pair of electrodes being associated with a second orientation of the device;

a conductive material in the internal chamber; and a filling in the internal chamber configured to restrict an open volume of the internal chamber such that the conductive material is guided through a particular path defined by the filling;

wherein effects of gravity cause the conductive material to be guided through the particular path such that a first circuit between the first pair of electrodes is completed by the conductive material when the device is oriented in the first orientation;

wherein effects of gravity cause the conductive material to be guided through the particular path such that a second circuit between the second pair of electrodes is completed by the conductive material when the device is oriented in the second orientation;

wherein effects of gravity cause the conductive material to be guided through the particular path such that the first circuit between the first pair of electrodes is not completed when the device is not oriented in the first orientation; and wherein effects of gravity cause the conductive material to be guided through the particular path such that the second circuit between the second pair of electrodes is not completed when the device is not oriented in the second orientation;

securing the device to the subject such that the device is placed in the first orientation when the subject is in a first body orientation and such that the device is placed in a second orientation when the subject is in a second body orientation; and determining the body orientation of the subject based on a reading from the first pair of electrodes and based on a reading from the second pair of electrodes.

7. The method of claim 6, wherein the subject is a human.

8. The method of claim 7, wherein the human is no more than three years old.

9. The method of claim 7, wherein the device is secured to an anatomical region of the human.

10. The method of claim 6, wherein said step of securing the device comprises the use of an adhesive on the subject.

11. The method of claim 10, wherein the device comprises the adhesive.

12. The method of claim 6, wherein the first and second pairs of electrodes are spaced from one another such that a rotation of the device on an axis of rotation by at least 30 degrees is necessary to transition the device from the first orientation to the second orientation.

13. The method of claim 6, wherein the first and second pairs of electrodes are disposed on an internal surface which bounds the internal chamber.

14. The method of claim 6, wherein the device further comprises:

a battery; and an alarm;

wherein the alarm is operative to sound in response to one or more of: the first circuit being connected for at least a prescribed portion of a prescribed time period, a battery level of the battery falling below a threshold value.

15. The method of claim 14, wherein the prescribed time period is at least 2 hours.

16. The method of claim 14, wherein the method further comprises a step of changing the body orientation of the subject after the alarm sounds in response to the first circuit being connected for at least a prescribed portion of a prescribed time period.

17. The method of claim 6, wherein the device further comprises:

a communication link;

wherein the method further comprises the step of:

transmitting a signal based on the reading from the first pair of electrodes to an external device.

18. The method of claim 17, wherein the external device is operative to trigger a warning in response to receiving the signal.

* * * * *